US006880968B1

(12) United States Patent
Haar

(10) Patent No.: US 6,880,968 B1
(45) Date of Patent: Apr. 19, 2005

(54) TEST ELEMENT ANALYSIS SYSTEM

(75) Inventor: Hans-Peter Haar, Wiesloch (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 10/111,626

(22) PCT Filed: Oct. 26, 2000

(86) PCT No.: PCT/DE00/03804

§ 371 (c)(1),
(2), (4) Date: Apr. 26, 2002

(87) PCT Pub. No.: WO01/33214

PCT Pub. Date: May 10, 2001

(30) Foreign Application Priority Data

Oct. 29, 1999 (DE) .......................................... 199 52 215

(51) Int. Cl.[7] .............................. G01K 1/16; G01J 5/00; A61B 5/00
(52) U.S. Cl. ........................ 374/131; 374/142; 600/549; 436/147
(58) Field of Search ................................. 374/121, 123, 374/128, 132, 135, 141–142, 120, 163, 165, 208; 600/316, 473, 474, 547, 549, 309–310, 347, 368; 436/147

(56) References Cited

U.S. PATENT DOCUMENTS

| | | | |
|---|---|---|---|
| 4,360,723 A | * 11/1982 | Fukuda et al. | |
| 4,372,682 A | 2/1983 | Nenninger | ................... 356/244 |
| 4,720,372 A | 1/1988 | Fey et al. | ...................... 422/67 |
| 4,947,850 A | * 8/1990 | Vanderkooi et al. | |
| 4,988,211 A | * 1/1991 | Barnes et al. | |
| 4,993,419 A | * 2/1991 | Pompei et al. | |
| 5,035,862 A | 7/1991 | Dietze et al. | ............... 422/68.1 |
| 5,095,913 A | * 3/1992 | Yelderman et al. | ......... 128/719 |
| 5,313,941 A | * 5/1994 | Braig et al. | .................. 128/633 |

(Continued)

FOREIGN PATENT DOCUMENTS

| | | | |
|---|---|---|---|
| DE | 3321783 A1 | 12/1984 | .......... G01N/33/52 |
| EP | 0801926 A1 | 10/1997 | ............ A61B/5/00 |
| EP | 0851229 A1 | 7/1998 | ......... G01N/33/543 |
| EP | 0943912 A1 | 9/1999 | .......... G01N/21/35 |
| JP | 56160640 | 12/1981 | |
| JP | 10142066 | 5/1998 | |
| JP | 10150031 A | * 6/1998 | ........... H01L/21/31 |
| JP | 10206411 | 8/1998 | |
| JP | 10227699 | 8/1998 | |
| JP | WO 99/06822 | 2/1999 | .......... G01N/21/78 |
| WO | WO 9522928 | * 8/1995 | |

Primary Examiner—Gail Verbitsky
(74) Attorney, Agent, or Firm—Jill L. Woodburn; Richard T. Knauer; Sujatha Subramaniam

(57) ABSTRACT

Test element analysis system (1) for the analytical investigation of a sample (8), in particular of a body liquid, of human beings or of animals, comprising test elements (3) with a test zone (7), to be brought in contact with the sample to be investigated for the purpose of performing an analysis, in order to measure a measurement quantity characteristic for the analysis, and an evaluation instrument (2) with a test element holder (5) for positioning a test element (3) in a measuring position in order to perform a measurement, and a measurement and evaluation electronics (15) for measuring the characteristic change and for determining a result of the analysis, based on the result of the measurement.

In order to provide increased measuring accuracy by improved temperature compensation, it is proposed, in the scope of the invention, that the evaluation instrument (2) for the determination of the temperature prevailing in the test zone (7) of the test element (3) comprises an infrared detector (20).

30 Claims, 2 Drawing Sheets

U.S. PATENT DOCUMENTS

| | | | | |
|---|---|---|---|---|
| 5,405,511 | A | | 4/1995 | White et al. .............. 204/153.1 |
| 5,578,499 | A | | 11/1996 | Ismail ........................ 436/524 |
| 5,626,139 | A | * | 5/1997 | Szeles et al. ................ 128/664 |
| 5,820,264 | A | | 10/1998 | Tsao et al. ................... 374/131 |
| 5,823,966 | A | * | 10/1998 | Buchert |
| 5,972,715 | A | | 10/1999 | Celentano et al. ............ 436/46 |
| 6,066,243 | A | * | 5/2000 | Anderson et al. ........... 204/403 |
| 6,084,660 | A | * | 7/2000 | Shartle ........................ 356/39 |
| 6,087,182 | A | * | 7/2000 | Jeng et al. .................... 436/66 |
| 6,133,552 | A | * | 10/2000 | Saulnier et al. |
| 6,136,610 | A | * | 10/2000 | Polito et al. ................. 436/514 |
| 6,167,290 | A | * | 12/2000 | Yang et al. .................. 600/322 |
| 6,201,245 | B1 | * | 3/2001 | Schrader |
| 6,216,096 | B1 | * | 4/2001 | Obermeier |
| 6,261,519 | B1 | * | 7/2001 | Harding et al. ............... 422/58 |
| 6,302,855 | B1 | * | 10/2001 | Lav et al. .................... 600/584 |
| 6,320,170 | B1 | * | 11/2001 | Jennings et al. |
| 6,424,849 | B1 | * | 7/2002 | Berman et al. |
| 6,475,805 | B1 | * | 11/2002 | Charm et al. ................ 436/514 |
| 6,518,034 | B1 | * | 2/2003 | Phillips et al. ................. 435/14 |
| 6,541,266 | B1 | * | 4/2003 | Modzelewski et al. ........ 436/95 |
| 6,635,167 | B1 | * | 10/2003 | Batman et al. .............. 205/775 |
| 6,670,192 | B1 | * | 12/2003 | Galen et al. ................... 422/67 |
| 6,678,542 | B1 | * | 1/2004 | Braig et al. .................. 600/316 |
| 2002/0048307 | A1 | * | 4/2002 | Schmidt |
| 2002/0128543 | A1 | * | 9/2002 | Leonhardt .................... 600/316 |
| 2003/0050541 | A1 | * | 3/2003 | Wuori |
| 2003/0176183 | A1 | * | 9/2003 | Drucker et al. ........... 455/414.1 |
| 2004/0147034 | A1 | * | 7/2004 | Gore et al. .................... 436/95 |
| 2004/0186365 | A1 | * | 9/2004 | Jin et al. ..................... 600/365 |
| 2004/0236244 | A1 | * | 11/2004 | Allen et al. ................. 600/532 |

* cited by examiner

TEST ELEMENT ANALYSIS SYSTEM

The invention relates to a test element analysis system for the analytical investigation of a sample, in particular a body liquid, of human beings or of animals. The system consists of two components, namely test elements, comprising a test zone to which the sample to be investigated is contacted in order to perform an analysis by measuring a measurement quantity characteristic for the analysis, and an evaluation instrument with a test element holder for positioning a test element in a measuring position for making the measurement, and with a measuring and evaluation electronics for measuring the characteristic measurement quantity and deriving an analytical result therefrom.

Test element analysis systems are common in medical science, in particular for the analysis of blood and urine. In most cases, the test elements have the form of test strips. Other forms of test elements are, however, also common, e.g. flat, almost square plates.

Generally, the test elements contain reagents the reaction of which with the sample leads to a physically detectable change of the test element. This change is measured with the evaluation instrument belonging to the system. In particular, photometrical analysis systems are common, using test elements in which the reaction causes a color change of a detection layer which is measured photometrically. Furthermore, electrochemical analysis systems are of important significance. Here an electrically measurable change of the test element, in form of a voltage or a current, occurs due to the reaction. In addition to these analysis systems working with reagents, reagent-free analysis systems are also discussed, in which an analytically characteristic property (e.g. the light absorption spectrum) of the sample itself is measured after bringing the test element in contact with the sample. The invention is generally applicable to all these methods.

Test element analysis systems are to some extent used in medical laboratories. The invention is, however, particularly intended for application cases in which the patients themselves perform the analysis in order to monitor his or her health state (home monitoring). This is of particular medical importance for diabetics, who have to check their blood glucose concentration several times a day in order to adjust the insulin injections accordingly. For such purposes, the evaluation instruments must be light-weight, small, battery-operated and robust.

A fundamental problem is caused by the fact that the measured quantity which is characteristic for the analysis, is often very temperature-dependent. This temperature dependence is, in many cases, about one or two percent per degree. In the area of home-monitoring, the exposure of the analysis system to large temperature changes is unavoidable. Temperature variations of at least ±5% have to be taken into account. Much higher temperature variations may occur, however, e.g. if measurements under unusual conditions (in the car or outdoors) are required.

In order to avoid the measurement uncertainties resulting therefrom, it was proposed to temper the test zone of the test element by means of a corresponding thermostating device, in order to provide a defined, constant temperature. For example, U.S. Pat. No 5,035,862 describes the tempering of individual test fields of urine test strips by means of inductive heating. Another example, for a blood analysis instrument, is described in DE 3321783 A1. Such methods are, however, due to their high energy consumption, not practicable for small battery-operated instruments.

In some analysis systems, the temperature is determined electrically (by means of a thermocouple or a thermal resistor) at the time of the measurement in the housing of the evaluation instrument, and the measured temperature is taken into account for the determination of the analysis result. An example is described in WO 99/06822. Such a correction can be exact if the temperature in the environment of the evaluation instrument and the test element did not change significantly for an extended period before the measurement, so that the actual temperature of the sample in the measuring position almost equals to the electrically measured temperature. In particular in the field of home-monitoring, however, this condition is not always given, as the life circumstances of the patient require analyses to be performed at different places and with changing temperature conditions.

In order to solve this problem, U.S. Pat. No. 5,405,511 proposes to measure the temperature repeatedly in regular intervals, and to determine the corrective temperature by extrapolation based on the temperature history measured over a certain period of time. This, however, requires a permanent determination of the temperature, continuously or in certain intervals, over a period of several minutes before the analysis. In order to avoid the resulting waiting time before the test, temperature measurements are, according to U.S. Pat. No. 5,405,511, also performed when the instrument is switched off in intervals of several minutes. This allows to make the extrapolation to the corrective temperature immediately after the instrument is switched on. This method, however, causes an increased battery consumption, as the electronic system of the instrument must be put into operation in intervals of several minutes, in order to determine the temperature. Furthermore, the estimation of the corrective temperature by means of an extrapolation algorithm is not reliable under all operating conditions. EP 0851229 A1 describes an analysis system in which a temperature measuring surface coated with a thermo-chromous liquid crystal (TLC) is located at the holder of the test element or at the test element itself. The temperature of the TLC is determined by photometrical measurement. Here, good correspondence of the measurement with the actual temperature of the test zone can only be achieved if the test element itself is coated with the TLC. This, however, leads to considerable additional cost for the production of the test elements. Furthermore, an acceptable accuracy of the temperature measurement can only be achieved with high expense for the measurement technology.

The invention addresses the problem to provide a test element analysis system which provides an increased measurement accuracy by an improved temperature compensation. This should be achieved with low expense, as appropriate for home-monitoring systems.

In a test element analysis system of the previously described type the problem is solved by providing the evaluation instrument with an infrared detector for the determination of the temperature in the test zone of the test element.

The particular requirements of common test strip analysis systems have the disadvantage that in most cases it is not possible to position an infrared detector in such a manner that it directly detects the infrared radiation coming from the test zone with sufficient selectivity and sensitivity in order to ensure the required exactness of the temperature measurement. According to a preferred embodiment of the invention this problem is solved by providing a connection of the test zone and the infrared detector by a location-selective infrared radiation transport device fulfilling the following requirements:

It selectively transmits the IR radiation emerging from the test zone to the detector.

A very high share of the IR radiation emerging from the test zone arrives at the deetector, i.e. the transport device works almost loss-free.

Principally, these requirements can be fulfilled with an optical imaging system which comprises at least one lens. Substantially preferred components of the infrared transport device are, however, a hollow conductor with IR-reflecting interior walls, in particular made of metal-coated plastics, and/or an imaging mirror located inside the housing. These elements allow an almost loss-free IR transport from the test zone to the infrared detector, as well as a very good selectivity. The cost is low, and it is possible, without any problems, to provide a curved or polygonal (non-straight) radiation path between the test zone and the infrared detector. This allows a realization of the infrared temperature measurement of the test zone, which is optimally adapted to the requirements of a test element analysis system.

The invention is hereafter described in more detail with reference to exemplary embodiments shown in the figures. The described features can be used single or in combination in order to create preferred embodiments of this invention.

Figure 1:
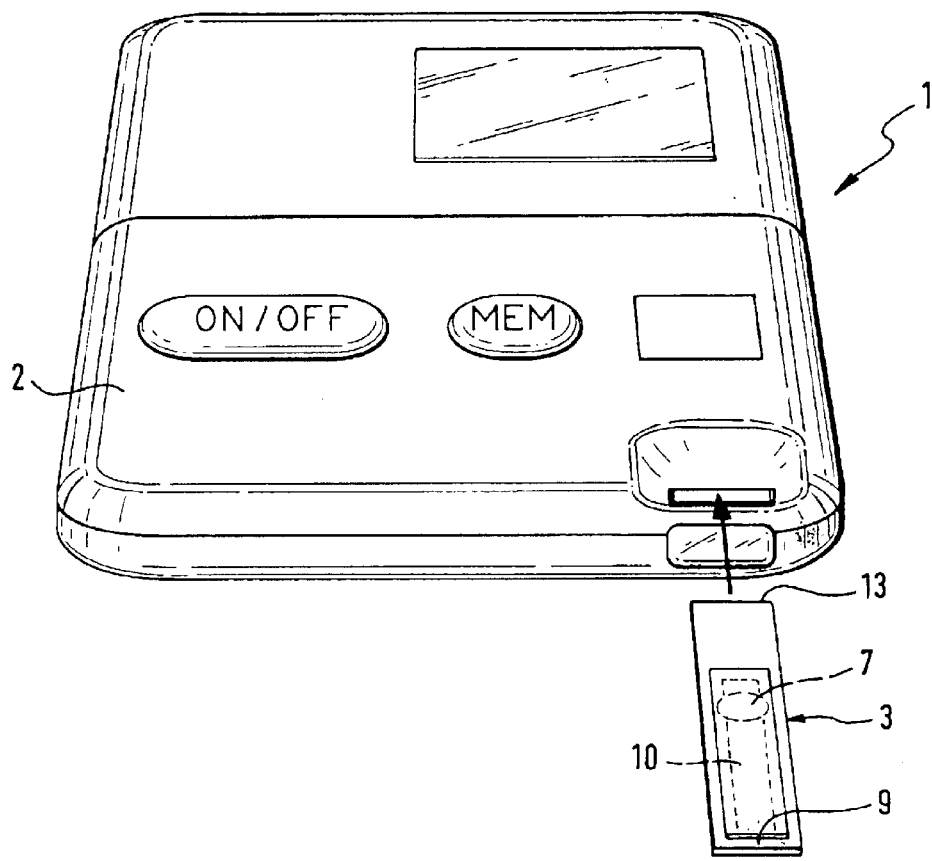
FIG. 1 shows a test element analysis system according to the invention.
Figure 2:
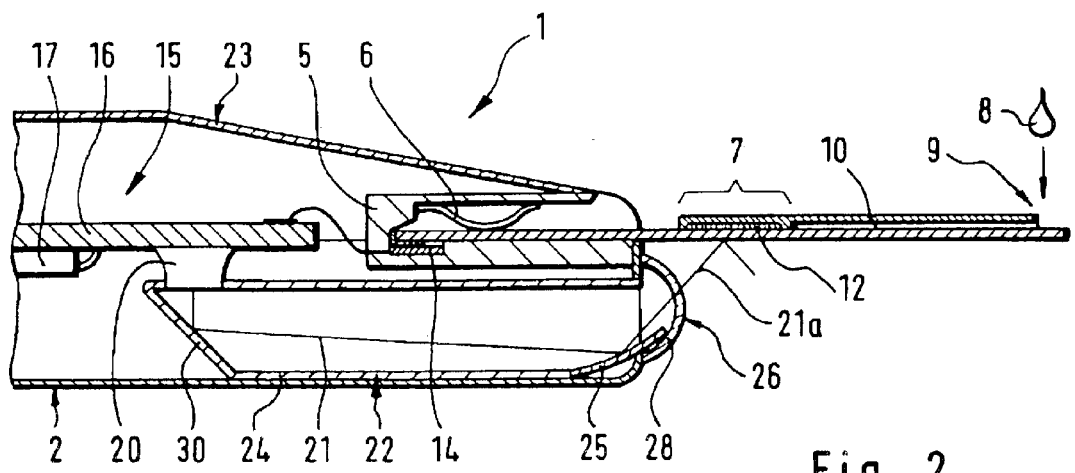
FIG. 2 shows a partial sectional view of an analysis system according to the invention.

The analysis system shown in FIGS. 1 and 2 consists of an evaluation instrument 2 and of disposable test elements 3 for single use.

The evaluation instrument 2 has a test element holder 5 for fixing a test element 3 in the measuring position shown in FIG. 2. The test element 3 is fixed in the measuring position by appropriate means, as e.g. a leaf spring 6.

For making a measurement, the sample liquid (e.g. blood) has to be contacted to a measurement zone 7. In the shown embodiment of a test element this is achieved by applying a blood drop 8 to a sample application zone 9 located at the end of the test element 3 from where it is suctioned to the measurement zone 7 through a capillary gap 10. A reagent layer 12, to be dissolved by the sample liquid and reacting with its components, is located in the measurement zone 7.

The reaction leads to a measurable change in the measurement zone 7. In the shown case of an electrochemical test element, the measurement of an electrical measurement quantity is performed by means of electrodes located in the measurement zone (not shown in the figure) connected to contact stripes 13. In the measuring position, the contact stripes 13 establish an electrical contact to corresponding countercontacts 14 of the test element holder 5 which again are connected to a measuring and evaluation electronics 15. The measuring and evaluation electronics 15 is highly integrated for compact design and high reliability. In the shown case, it essentially consists of a printed circuit board 16 and a special IC (ASIC) 17.

An infrared detector 20 for the determination of the temperature in the test zone 7 is also mounted on the printed circuit board 16. Appropriate infrared detectors are inexpensively available. Preferably, a detector type including an integrated temperature sensor for self-calibration (e.g. a NTC semiconductor element) is chosen.

Generally it is advantageous if the infrared detector 20 is integrated into the measuring and evaluation electronics 15 in such a manner that a rigid mechanic connection is provided between the infrared detector 20 and the further components of the measuring and evaluation electronics 15. Short and mechanically rigid conductor connections between the infrared detector 20 and the further components of the measuring and evaluation electronics 15 do not only allow a compact design, but also provide high mechanic and electrical stability as well as a good long-term reliability.

At first glance it seems disadvantageous that the transmission path shown in dotted line in FIG. 2 which the IR radiation must travel from the test zone 7 to the infrared detector 20 is relatively long and not straight. This is particularly true if the evaluation instrument has a very flat design which is desirable (for easy handling) in practical use, but does not allow to arrange the test element holder 5 above the electronic unit 15.

Additional problems arise if the test element and the holder of the evaluation instrument are formed—as shown—in such a manner that the test element 3, when in the measuring position, sticks out of the housing 23 of the evaluation instrument 2. Such a design is advantageous for the handling of the analysis system, since the sample can be provided to the test zone 7 while the test element is already in the measuring position. However, for the determination of the temperature in the test zone 7, this implies the disadvantage that the transmission path 21 must pass through a window 26 arranged in the housing 2 and including a section 21a located outside the housing 23.

The infrared transport device, designated as 22, enables even in such difficult cases a selective and sensitive detection of the infrared radiation coming from the test zone 7. In the shown case, it consists of a hollow conductor 24 with IR-reflecting interior walls, and an imaging mirror 25 located inside the housing 23 of the evaluation instrument 2.

The hollow conductor 24 is made from a plastic part which is at least in its interior metal-coated. (in particular, gold-plated). By means of this hollow conductor 24, the desired IR transmission path 21 can be realized within the housing 25, in a simple and inexpensive way.

If—as in case of the shown test element analysis system—the IR transmission path 21 includes a section 21a located outside the housing 25 of the evaluation instrument 2, it is advantageous to realize in this section the necessary selective detection of the IR radiation coming from the test zone 7 by means of an optical imaging system. Preferably a concave imaging mirror 25 as shown in FIG. 2 is used. The optical window 26 is closed dust-proof, preferably with a pane 28 transparent for infrared radiation, in particular a polyethylene sheet.

Figure 3:
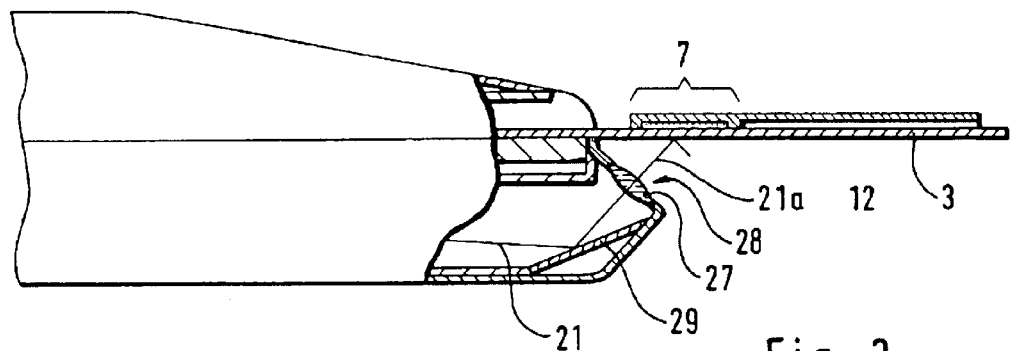
FIG. 3 shows a partial sectional view of an alternative embodiment.

FIG. 3 shows an alternative embodiment in which the optical imaging system is formed by an optical lens integrated into the pane 28, whereas the required beam deflection of the IR radiation on the transmission path 21 is provided by a plane mirror 29.

In the embodiments shown in FIGS. 2 and 3, the function of the location-selective light transport device 22 is essentially based on the effect of an optical imaging system realized by the imaging mirror 25 or the lens 27. Inside hollow conductor 24 the light path is mainly influenced by the rear, inclined surface which acts as a plane mirror 30 and essentially effects the required deflection to the IR detector 20.

Figure 4:
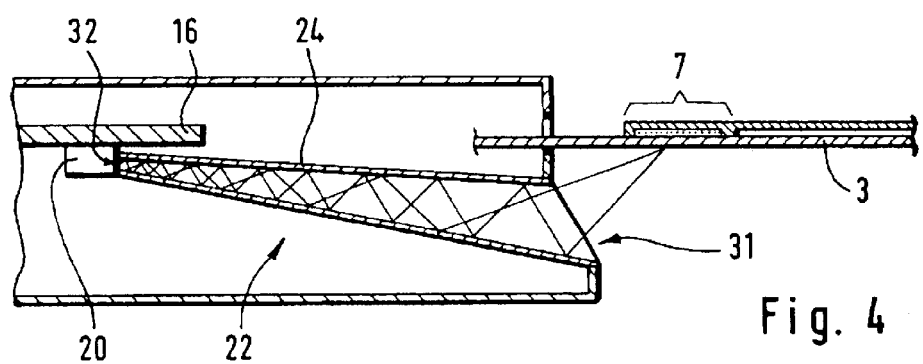
FIG. 4 shows a diagrammatic sectional view of a further alternative embodiment.
Figure 5:
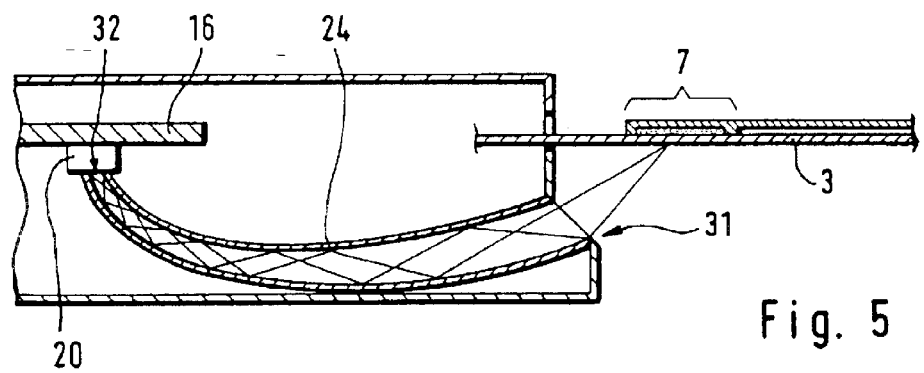
FIG. 5 shows a diagrammatic sectional view of a third alternative embodiment.

A very effective and at the same time very inexpensive realization of the location-selective IR transport device can be provided (even without an optical imaging system) by means of a hollow conductor with mirror-coated interior, which is designed in such a manner—as shown in FIGS. 4 and 5—that the input opening 31 facing the test zone 7 has a larger opening cross-section than the output opening 32 facing the infrared detector. In such an embodiment it is advantageous if the hollow conductor 24 tapers continuously between the input opening 31 and the output opening 32, i.e. its cross-section decreases gradually along the path. In this way a concentration of the infrared radiation intensity reflected at the interior walls of the hollow conductor 24 is provided.

In the embodiment shown in FIG. 4, the axis of hollow conductor 24 is a straight line. In this case, the light-sensitive surface of the detector 20 is located in a lateral position. However, it is easily possible to produce the hollow conductor 24 in a curved embodiment, as shown in FIG. 5. Such a curved-embodiment enables a particularly flexible design and positioning of the test element 3 with the test zone 7 and of the printed circuit board 16 with the detector 20.

Although FIGS. 4 and 5 do not show an optical imaging system, it is of course possible to combine a hollow conductor 24 of the construction type shown in the figures, with an optical imaging system in form of a lens or in form of an imaging mirror.

What is claimed is:

1. Test element analysis system for the analytical investigation of an analyte present in a body liquid of humans or animals, comprising
   at least one test element with a test zone, which is contacted with a sample to be analyzed in order to measure a measurement quantity which is characteristic for the analysis, and
   an evaluation instrument with a test element holder for positioning at least one test element in a measuring position in order to perform a measurement, an analyte measurement and evaluation electronics for measuring the characteristic change and for determining, based on this measurement, a result of the analysis, and an infrared detector adapted for the determination of the temperature in the test zone,
   characterized in that the evaluation instrument comprises an infrared radiation transport device for providing a location-selective connection of the test zone with the infrared detector.

2. Analysis system according to claim 1, characterized in that the infrared detector is integrated into the measuring and evaluation electronics.

3. The system of claim 2 wherein a rigid mechanic connection is provided the infrared detector and the measuring and evaluation electronics.

4. Analysis system according to claim 1, characterized in that the infrared radiation transport device comprises a hollow conductor with an interior wall reflective for infrared radiation.

5. Analysis system according to claim 4, characterized in that the hollow conductor is made from metal-coated plastic.

6. Analysis system according to claim 4, characterized in that an input opening of the hollow conductor facing the test zone has a larger opening cross-section than an output opening of the hollow conductor facing the infrared detector.

7. Analysis system according to claim 1, characterized in that the location-selective infrared radiation transport device includes an imaging mirror located inside a housing of the evaluation instrument.

8. Analysis system according to claim 1, characterized in that
   the test element, in the measuring position, sticks out of a housing of the evaluation instrument in such manner that the sample can be contacted to the test zone, while the test element is in the measuring position,
   the detector is located in a housing of the evaluation instrument,
   the housing of the evaluation instrument comprises a window which is transparent for infrared radiation, and
   a transport path of the infrared radiation between the test zone and the infrared detector passes through the optical window.

9. Analysis system according to claim 8, characterized in that the optical window is dust-proof closed by means of a pane transparent to infrared radiation.

10. Analysis system according to claim 8, characterized in that the evaluation instrument comprises an infrared radiation transport device for providing a location-selective connection of the test zone with the infrared detector and the infrared transparent radiation pane of the optical window is combined with an optical lens forming a part of the infrared radiation transport device.

11. Analysis system according to claim 8, characterized in that the pane is a polyethylene foil.

12. The system of claim 1 wherein the measuring and evaluation electronics includes a circuit board and the infrared detector is mounted on the circuit board.

13. Test element analysis system for an analytical investigation of a sample, the system comprising
   a test element with a test zone, which is contacted with the sample to be analyzed in order to measure a measurement quantity characteristic for the analysis, and
   an evaluation instrument including a test element holder formed to position the test element in a measuring position to perform a measurement, an infrared detector to determine a temperature of the test zone, and a measurement and evaluation electronics formed to measure a characteristic change and to determine, based on this measurement, a result of the analysis, wherein the evaluation instrument comprises an infrared radiation transport device formed to provide a location-selective connection of the test zone with the infrared detector, and
   wherein the infrared radiation transport device comprises a hollow conductor with an interior wall reflective for infrared radiation.

14. The system of claim 13 wherein the infrared detector is integrated into the measuring and evaluation electronics.

15. The system of claim 13 wherein the hollow conductor is made from metal-coated plastic.

16. The system of claim 13 wherein an input opening of the hollow conductor facing the test zone has a larger opening cross-section than an output opening of the hollow conductor facing the infrared detector.

17. The system of claim 13 wherein the infrared radiation transport device includes an imaging mirror.

18. The system of claim 17 wherein the imaging mirror is located inside the evaluation instrument.

19. The system of claim 13 wherein the test element, in the measuring position, sticks out of the evaluation instrument in such a manner that the sample can be contacted to the test zone, while the test element is in the measuring position.

20. The system of claim 19 wherein the infrared detector is located in a housing of the evaluation unit.

21. The system of claim 19 wherein a housing of the evaluation instrument comprises a window that is transparent for infrared radiation.

22. The system of claim 21 wherein a transport path of infrared radiation between the test zone and the infrared detector passes through the window.

23. The system of claim 21 wherein the evaluation instrument comprises the infrared radiation transport device for providing a location-selective connection of the test zone with the infrared detector and an infrared transparent radiation pane of the window is combined with an optical lens forming a part of the infrared radiation transport device.

24. The system of claim 21 wherein the window is closed by a polyethylene foil.

25. Test element analysis system for an analytical investigation of a sample, the system comprising
- a test element with a test zone, which is contacted with the sample to be analyzed in order to measure a measurement quantity characteristic for the analysis, and
- an evaluation instrument including a test element holder formed to position the test element in a measuring position to perform a measurement, an infrared detector to determine a temperature of the test zone, and a measurement and evaluation electronics formed to measure a characteristic change and to determine, based on this measurement, a result of the analysis,
- wherein the test element, in the measuring position, sticks out of the evaluation instrument in such a manner that the sample can be contacted to the test zone, while the test element is in the measuring position, a housing of the evaluation instrument comprises a window that is transparent for infrared radiation, and the window is closed by pane transparent to infrared radiation, wherein a transport path of infrared radiation between the test zone and the infrared detector passes through the window.

26. Test element analysis system for the analytical investigation of a body liquid of humans or animals, comprising
- at least one test element which contains at least one reagent, the reaction of which with the sample liquid leads to a detectable change of a measurement quantity which is characteristic of the analysis, the test element comprising a test zone, which is contacted with the sample to be analyzed in order to measure a measurement quantity which is characteristic for the analysis, and
- an evaluation instrument with a test element holder for positioning at least one test element in a measuring position in order to perform a measurement, a measurement and evaluation electronics for measuring the characteristic change and for determining, based on this measurement, a result of the analysis, and an infrared detector adapted for the determination of the temperature in the test zone, characterized in that the evaluation instrument comprises an infrared radiation transport device for providing a location-selective connection of the test zone with the infrared detector.

27. Analysis system according to claim 26, characterized in that the infrared radiation transport device comprises a hollow conductor with an interior wall reflective for infrared radiation.

28. Analysis system according to claim 27, characterized in that the hollow conductor is made from metal-coated plastic.

29. Analysis system according to claim 27, characterized in that an input opening of the hollow conductor facing the test zone has a larger opening cross-section that an output opening of the hollow conductor facing the infrared detector.

30. Analysis system according to claim 26, characterized in that the location-selective infrared radiation transport device includes an imaging mirror located inside a housing of the evaluation instrument.

* * * * *